(12) United States Patent
Qian et al.

(10) Patent No.: US 8,691,977 B2
(45) Date of Patent: Apr. 8, 2014

(54) CERTAIN CHEMICAL ENTITIES, COMPOSITIONS, AND METHODS

(75) Inventors: Xiangping Qian, Foster City, CA (US); Yong-Liang Zhu, Fremont, CA (US)

(73) Assignee: Neupharma, Inc., Foster City, CA (US)

( * ) Notice: Subject to any disclaimer, the term of this patent is extended or adjusted under 35 U.S.C. 154(b) by 204 days.

(21) Appl. No.: 13/215,120

(22) Filed: Aug. 22, 2011

(65) Prior Publication Data

US 2012/0052019 A1    Mar. 1, 2012

Related U.S. Application Data

(60) Provisional application No. 61/376,238, filed on Aug. 23, 2010.

(51) Int. Cl.
| | |
|---|---|
| *C07J 53/00* | (2006.01) |
| *C07D 207/00* | (2006.01) |
| *C07D 241/04* | (2006.01) |
| *C07D 295/00* | (2006.01) |
| *A01N 35/00* | (2006.01) |
| *A01N 33/02* | (2006.01) |
| *A61K 31/535* | (2006.01) |
| *A61K 31/40* | (2006.01) |

(52) U.S. Cl.
USPC ............. 540/47; 548/528; 544/380; 544/154; 514/691; 514/659; 514/237.5; 514/428; 514/238.8

(58) Field of Classification Search
None
See application file for complete search history.

(56) References Cited

U.S. PATENT DOCUMENTS 5,846,514 A    12/1998    Foster et al.
6,334,997 B1    1/2002    Foster et al.

FOREIGN PATENT DOCUMENTS

CN    101798333 A    8/2010

OTHER PUBLICATIONS

Figueiredo et al., "Novel Quinone Methides from *Salacia kraussii* with in Vitro Antimalarial Activity", 1998, American Chemical Society, Journal of Natural Products (1998), 61(6), 718-723.*
World Health Organization, Guidelines on packaging for pharmaceutical products, 2002, WHO Technical Report Series, No. 902.128-30.*
Allison, et al. Central Nervous System Effects of Celastrol, a Potent Antioxidant and Antiinflammatory Agent. CNS Drug Reviews. 2000 6(1):45-62.
Evans. Synthesis of radiolabeled compounds, J. Radioanal. Chem. 1981; 64(1-2):9-32.
International search report and written opinion dated Dec. 1, 2011 for PCT/CN2011/001391.
Jin, et al. Antiinflammatory constituents of *Celastrus orbiculatus* inhibit the NF-kappaB activation and NO production. J Nat Prod. Jan. 2002;65(1):89-91.
Johnson, et al. 536. Pristimerin. Part IV. Total structure. Chem. Soc., 1963; 2884-2889.
Kalbalka, et al. The Synthesis of Radiolabeled Compounds via Organometallic Intermediates, Tetrahedron. 1989; 45(21):6601-21.
Martinod, et al. Isolation of tingenon and prostomerin from *Maytenus chuchuhuasca*. Phytochemistry. 1976; 15:562-563.
Monache, et al. New Triterpene Quinone-methides from Hippocrateaceae. J. Chem. Soc. Perkin I. 1979; 3127-3131.

* cited by examiner

*Primary Examiner* — James O Wilson
*Assistant Examiner* — Oluwafemi Masha
(74) *Attorney, Agent, or Firm* — Wilson Sonsini Goodrich & Rosati

(57) ABSTRACT

Chemical entities which are triterpenoid derivatives, pharmaceutical compositions and methods of treatment of inflammatory, neurodegenerative, neoplastic and autoimmune diseases are described.

24 Claims, No Drawings

CERTAIN CHEMICAL ENTITIES, COMPOSITIONS, AND METHODS

This application claims the benefit of priority to U.S. provisional patent application 61/376,238, filed Aug. 23, 2010, which is incorporated herein by reference in its entirety.

Provided are certain chemical entities, pharmaceutical compositions and methods for the treatment of inflammatory, neurodegenerative, neoplastic and autoimmune diseases.

Numerous molecular and cellular events are associated with inflammatory disease processes. Such events may be defensive in the control or suppression of such processes, or may enhance inflammation to the detriment of the organism. Inflammation is a defense reaction against diverse insults, designed to remove noxious agents and to inhibit their detrimental effects. It consists of a dazzling array of molecular and cellular mechanisms and an intricate network of controls to keep them in check. The promotion of defensive mechanisms and the suppression of pro-inflammatory stimuli is the basis of therapy in the treatment of inflammatory, neurodegenerative, and neoplastic diseases.

In neurodegenerative diseases, inflammation may be triggered by the accumulation of proteins with abnormal conformations or by signals emanating from injured neurons. The pathogenesis of Alzheimer's disease is associated with: activation of microglia and the production of TNF-α, IL-β, and superoxide. Also expressed is an inducible isoform of NO synthase which releases high levels of NO. In the presence of superoxide, NO forms peroxynitrite which damages neurons and other cell types.

A substantial body of evidence supports the conclusion that chronic inflammation can predispose an individual to cancer, as demonstrated by the association between chronic inflammatory bowel diseases and the increased risk of colon carcinoma. Chronic inflammation is caused by a variety of factors, including bacterial, viral, and parasitic infections, chemical irritants, and nondigestible particles. The longer the inflammation persists, the higher the risk of associated carcinogenesis.

In some diseases, however, the body's defense system (immune system) inappropriately triggers an inflammatory response when there are no foreign substances to fight off. In these diseases, called autoimmune diseases, the body's normally protective immune system causes damage to its own tissues. The body responds as if normal tissues are infected or somehow abnormal. Some, but not all, types of arthritis are the result of misdirected inflammation. Arthritis is a general term that describes inflammation in joints. Some types of arthritis associated with inflammation include: Rheumatoid arthritis, Shoulder tendinitis or bursitis, Gouty arthritis and Polymyalgia rheumatica.

Celastrol or tripterine is a red pigment isolated from the roots of both *T. wilfordii* and *Celastrus scandens*, as disclosed by Schechter et al, J. Am. Chem. Soc., vol. 64 (1942) at 182-183, incorporated herein as reference.

Celastrol is a member of a group of triterpene-type compounds called quinone-methides. Closely related compounds, tingenone and pristimerin, have been isolated from Maytenus chuchuhuasca Raymond Hamet, a plant which has been used in Ecuador for skin cancer treatment (P. Martinod, A. Paredes, F. D. Monache and G. B. Marini-Bettolo, Phytochemistry, Vol. 15 (1976), 562-563).

The isolation and characterization of some related quinone-methides, including pristimerin, has been reported by Monache et al. (J. Chem. Soc. Perkin I (1979) at 3127-3131). Some of these compounds also have anti-neoplastic effect.

Celastrol inhibits microglial activation, the production of TNF-α, IL-1β, and the expression of inducible NO synthase. Celastrol does not inhibit constitutive NO synthases which is required to maintain neuronal function and vascular perfusion (A C Allison, R Cacabelos, V R M Lombardi, X A Alvarez and C Vigo, CNS Drug Reviews 6: 45 (2000)). Celastrol has also been shown to be a potent inhibitor of both NF-KB activation and nitric oxide production at IC50's of 0.27 and 0.23 uM respectively. This activity is considerably more potent than that of the standard, aminoguanidine with an IC50 of 16 uM (H Z Jin, B Y Hwang, H S Kim, J H Lee, Y H Kim and J J Lee, J Nat Prod 65: 89 (2002)).

The in vivo anti-inflammatory effects of celastrol have been demonstrated in animal models of collagen-induced arthritis, systemic lupus erythematosus, and various tumors. Celastrol is also known to inhibit the proliferation of a variety of tumor cells, including those from leukemia, gliomas, and prostate cancer. The ability of celastrol to modulate the expression of proinflammatory cytokines, MHC-II antigen, inducible nitric oxide (NO) synthase (iNOS), adhesion molecules in endothelial cells, proteasome activity, topoisomerase II, potassium channels, and heat shock response has been reported. Celastrol was found to inhibit cancer cell proliferation and induce leukemic cell death.

Celastrol has the potential to become a better therapeutic drugs for treating inflammatory, neurodegenerative, neoplastic and autoimmune diseases. However, celastrol has shown serious cellular toxicity and undesirable pharmacokinetic characteristics which has stifled development as useful drugs. With the belief that such toxicity and pharmacokinetic characteristics can be decreased and useful activities enhanced by structural modifications, we have explored such modifications by designing and synthesizing compounds related to celastrol that incorporate structural variations anticipated to provide a drug-like profile.

Provided is at least one chemical entity chosen from compounds of Formula I:

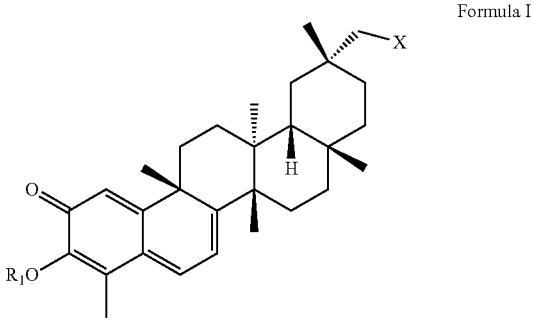

Formula I and pharmaceutically acceptable salts thereof, wherein $R_1$ is chosen from hydrogen, optionally substituted alkyl, optionally substituted acyl, optionally substituted aminocarbonyl, optionally substituted alkoxycarbonyl, —P(=O)(OR$^a$)(OR$^b$), and —C(R$^c$)(R$^d$)OP(=O)(OR$^a$)(OR$^b$), where R$^a$, R$^b$, R$^c$, and R$^d$ are independently chosen from hydrogen, optionally substituted alkyl, optionally substituted cycloalkyl, optionally substituted heterocycloalkyl, optionally substituted aryl, and optionally substituted heteroaryl;

X is chose from —OR$_2$ and —NR$_3$R$_4$;

$R_2$ is chosen from hydrogen, optionally substituted alkyl, optionally substituted aryl, optionally substituted cycloalkyl, optionally substituted heteroaryl, optionally substituted heteroclycloalkyl, optionally substituted acyl, optionally substituted aminocarbonyl, and optionally substituted alkoxycarbonyl;

$R_3$ is chosen from hydrogen, optionally substituted alkyl, optionally substituted aryl, optionally substituted cycloalkyl, optionally substituted heteroaryl, optionally substituted heteroclycloalkyl, optionally substituted acyl, optionally substituted aminocarbonyl, optionally substituted alkoxycarbonyl, and optionally substituted sulfonyl; and $R_4$ is chosen from hydrogen, optionally substituted alkyl, optionally substituted aryl, optionally substituted cycloalkyl, optionally substituted heteroaryl, optionally substituted heteroclycloalkyl, optionally substituted alkoxy, optionally substituted cycloalkyloxy, and optionally substituted heterocycloalkyloxy;

or $R_3$ and $R_4$ may optionally be joined together with any intervening atoms to form an optionally substituted heterocycloalkyl ring, provided that the compound of Formula I is not (6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one.

The chemical entities described herein may be used in treating a variety of inflammatory, neurodegenerative, neoplastic and autoimmune diseases including cancer, inflammatory diseases of the bowel; Crohn's disease; ulcerative colitis; cancer; cancers including: Alzheimer's disease; Parkinson's disease; Huntington's disease; autoimmune diseases including nephritis, rheumatoid arthritis, systemic lupus erythematosus, autoimmune diabetes mellitus and multiple sclerosis; organ and cellular transplant rejection; graft-versus-host disease; septic and traumatic shock; and in protecting selected tissues from damage due to irradiation of adjacent tissues.

Accordingly, also provided are methods of treating the conditions set forth in the preceding paragraph, by administering to a subject a therapeutically effective amount of at least one chemical entity described herein.

These and other objects and features of the invention will become more fully apparent when the following detailed description of the invention is read As used herein, the following words and phrases are generally intended to have the meanings as set forth below, except to the extent that the context in which they are used indicates otherwise.

A compound that is "substantially pure" refers to a compound having a purity of greater than 95% on a weight basis with respect to impurities stemming from synthesis of the compound or isolation of the compound from a natural (e.g. plant) source.

"Method of treating inflammatory, neurodegenerative, neoplastic and autoimmune diseases" encompasses treatment of a mammalian subject, particularly a human subject, and includes (i) arresting the development of clinical symptoms of the diseases, (ii) bringing about a regression in the clinical symptoms of the diseases, and/or (iii) prophylactic treatment for preventing the onset of the diseases.

The term "mammal" is intended to have its standard meaning, and encompasses humans, dogs, cats, sheep, and cows, for example.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

The following abbreviations and terms have the indicated meanings throughout:

c-=cyclo
Et=ethyl
EtOAc=ethyl acetate
EtOH=ethanol
g=gram
h or hr=hour
HPLC=high pressure liquid chromatography
i-=iso
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
min=minute
mL=milliliter
n-=normal
Ph=phenyl
quant.=quantitative
RP-HPLC=reverse phase-high pressure liquid chromatography
rt or RT=room temperature
s-=sec-=secondary
t-=tert-=tertiary
THF=tetrahydrofuran As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —$CONH_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "mono- and di-alkylcarboxamide" refers to a group of the formula —(C=O)NR$_a$R$_b$ wherein R$_a$ and R$_b$ are independently chosen from hydrogen and alkyl groups of the indicated number of carbon atoms, provided that R$_a$ and R$_b$ are not both hydrogen.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a C$_2$ acyl group is an acetyl group having the formula CH$_3$(C=O)—.

As used herein, "formyl" refers to the group —C(O)H.

As used herein, "carboxy" and/or "carboxyl" refer to the group —C(O)OH.

As used herein, "alkoxycarbonyl" refers to a group of the formula (alkoxy)(C=O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker.

As used herein, "acyloxy" refers to (acyl)-O—.

As used herein, "alkoxycarbonyloxy" refers to (alkoxycarbonyl)-O—.

As used herein, "azido" refers to the group —N$_3$.

As used herein, "amino" refers to the group —NH$_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —CONR$^b$R$^c$, where

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl, optionally substituted alkoxy; and R$^c$ is chosen from hydrogen and optionally substituted C$_1$-C$_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms chosen from O, N, and S in the heterocycloalkyl ring;

where each substituted group is independently substituted with one or more substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—NH$_2$.

As used herein, "substituted carbamimidoyl" refers to the group —C(=NR$^e$)—NR$^f$R$^g$ where R$^e$ is chosen from hydrogen, cyano, optionally substituted alkyl, optionally substituted cycloalkyl, optionally substituted aryl, optionally substituted heteroaryl, and optionally substituted heterocycloalkyl; and R$^f$ and R$^g$ are independently chosen from hydrogen optionally substituted alkyl, optionally substituted cycloalkyl, optionally substituted aryl, optionally substituted heteroaryl, and optionally substituted heterocycloalkyl, provided that at least one of R$^e$, R$^f$, and R$^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C1-C6 alkyl, optionally substituted aryl, and optionally substituted heteroaryl;

R$^b$ is chosen from H, optionally substituted C1-C6 alkyl, optionally substituted aryl, and optionally substituted heteroaryl; and R$^c$ is chosen from hydrogen and optionally substituted C1-C4 alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO2(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O$^-$) substituents, such as pyridinyl N-oxides.

As used herein, "heterocycloalkyl" refers to a single, non-aromatic ring, usually with 3 to 7 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteratoms independently chosen from oxygen, sulfur, and nitrogen and is not aromatic.

As used herein, "sulfanyl" refers to the groups: —S-(optionally substituted $(C_1-C_6)$alkyl), —S-(optionally substituted aryl), —S-(optionally substituted heteroaryl), and —S-(optionally substituted heterocycloalkyl). Hence, sulfanyl includes the group $C_1-C_6$ alkylsulfanyl.

As used herein, "sulfinyl" refers to the groups: —S(O)-(optionally substituted $(C_1-C_6)$alkyl), —S(O)-optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S(O$_2$)-(optionally substituted $(C_1-C_6)$alkyl), —S(O$_2$)-optionally substituted aryl), —S(O$_2$)-optionally substituted heteroaryl), —S(O$_2$)-(optionally substituted heterocycloalkyl), and —S(O$_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1-C_6$ alkyl, optionally substituted cycloalkyl, optionally substituted heterocycloalkyl, optionally substituted alkenyl, optionally substituted alkynyl, optionally substituted aryl, and optionally substituted heteroaryl; $R^b$ is chosen from hydrogen, optionally substituted $C_1-C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1-C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1-C_4$ alkyl, aryl, heteroaryl, aryl-$C_1-C_4$ alkyl-, hetero aryl-$C_1-C_4$ alkyl-, $C_1-C_4$ haloalkyl, —$OC_1-C_4$ alkyl, —$OC_1-C_4$ alkylphenyl, —$C_1-C_4$ alkyl-OH, —$OC_1-C_4$ haloalkyl, halo, —OH, —$NH_2$, —$C_1-C_4$ alkyl-$NH_2$, —$N(C_1-C_4$ alkyl)($C_1-C_4$ alkyl), —$NH(C_1-C_4$ alkyl), —$N(C_1-C_4$ alkyl)($C_1-C_4$ alkylphenyl), —$NH(C_1-C_4$ alkylphenyl), cyano, nitro, oxo (as a substituent for cycloalkyl or heterocycloalkyl), —$CO_2H$, —$C(O)OC_1-C_4$ alkyl, —$CON(C_1-C_4$ alkyl)($C_1-C_4$ alkyl), —$CONH(C_1-C_4$ alkyl), —$CONH_2$, —$NHC(O)(C_1-C_4$ alkyl), —$NHC(O)$ (phenyl), —$N(C_1-C_4$ alkyl)$C(O)(C_1-C_4$ alkyl), —$N(C_1-C_4$ alkyl)$C(O)$(phenyl), —$C(O)C_1-C_4$ alkyl, —$C(O)C_1-C_4$ alkylphenyl, —$C(O)C_1-C_4$ haloalkyl, —$OC(O)C_1-C_4$ alkyl, —$SO_2(C_1-C_4$ alkyl), —$SO_2$ (phenyl), —$SO_2(C_1-C_4$ haloalkyl), —$SO_2NH_2$, —$SO_2NH(C_1-C_4$ alkyl), —$SO_2NH$ (phenyl), —$NHSO_2(C_1-C_4$ alkyl), —$NHSO_2$ (phenyl), and —$NHSO_2(C_1-C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1-C_6$ alkyl, optionally substituted alkenyl, optionally substituted alkynyl, optionally substituted aryl, and optionally substituted heteroaryl;

$R^b$ is chosen from H, optionally substituted $C_1-C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1-C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1-C_4$ alkyl, aryl, heteroaryl, aryl-$C_1-C_4$ alkyl-, heteroaryl-$C_1-C_4$ alkyl-, $C_1-C_4$ haloalkyl, —$OC_1-C_4$ alkyl, —$OC_1-C_4$ alkylphenyl, —$C_1-C_4$ alkyl-OH, —$OC_1-C_4$ haloalkyl, halo, —OH, —$NH_2$, —$C_1-C_4$ alkyl-$NH_2$, —$N(C_1-C_4$ alkyl)($C_1-C_4$ alkyl), —$NH(C_1-C_4$ alkyl), —$N(C_1-C_4$ alkyl)($C_1-C_4$ alkylphenyl), —$NH(C_1-C_4$ alkylphenyl), cyano, nitro, oxo (as a substituent for cycloalkyl or heterocycloalkyl), —$CO_2H$, —$C(O)OC_1-C_4$ alkyl, —$CON(C_1-C_4$ alkyl)($C_1-C_4$ alkyl), —$CONH(C_1-C_4$ alkyl), —$CONH_2$, —$NHC(O)(C_1-C_4$ alkyl), —$NHC(O)$ (phenyl), —$N(C_1-C_4$ alkyl)$C(O)(C_1-C_4$ alkyl), —$N(C_1-C_4$ alkyl)$C(O)$(phenyl), —$C(O)C_1-C_4$ alkyl, —$C(O)C_1-C_4$ alkylphenyl, —$C(O)C_1-C_4$ haloalkyl, —$OC(O)C_1-C_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH (phenyl), —NHSO$_2$ (C$_1$-C$_4$ alkyl), —NHSO$_2$(phenyl), and —NHSO$_2$(C$_1$-C$_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH (phenyl), —NHSO$_2$(C$_1$-C$_4$ alkyl), —NHSO$_2$ (phenyl), and —NHSO$_2$(C$_1$-C$_4$ haloalkyl).

In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from —R$^a$, —R$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ halo alkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH (phenyl), —NHSO$_2$(C$_1$-C$_4$ alkyl), —NHSO$_2$ (phenyl), and —NHSO$_2$(C$_1$-C$_4$ haloalkyl).

As used herein, "substituted amino" refers to the group —NHR$^d$ or —NR$^d$R$^e$ wherein R$^d$ is chosen from hydroxy, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is chosen from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$ (phenyl), and —NHSO$_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable salts of compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, "pharmaceutically acceptable salts" includes "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is sp2-hybridized, an ether oxygen, or the oxygen of a sulfoxide or N-oxide.

The term "hydrogen bond donor" refers to an oxygen, nitrogen, or heteroaromatic carbon that bears a hydrogen.group containing a ring nitrogen or a heteroaryl group containing a ring nitrogen.

The compounds disclosed herein can be used in different enriched isotopic forms, e.g., enriched in the content of 2H, 3H, 11C, 13C and/or 14C. In one particular embodiment, the compound is deuterated at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH2)n-COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include NH2, primary, and secondary amines such as NHRx, and NRxRy, wherein Rx is hydrogen, (C1-C18)-alkyl, (C3-C7)-cycloalkyl, (C3-C7)-cycloalkyl-(C1-C4)-alkyl-, (C6-C14)-aryl which is unsubstituted or substituted by a residue (C1-C2)-alkyl, (C1-C2)-alkoxy, fluoro, or chloro; heteroaryl-, (C6-C14)-aryl-($C_1$-$C_4$)-alkyl- where aryl is unsubstituted or substituted by a residue ($C_1$-$C_2$)-alkyl, ($C_1$-$C_2$)-alkoxy, fluoro, or chloro; or heteroaryl-($C_1$-$C_4$)-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein the terms "group", "radical" or "fragment" are synonymous and are intended to indicate functional groups or fragments of molecules attachable to a bond or other fragments of molecules.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anticancer therapeutic.

As used herein, "significant" refers to any detectable change that is statistically significant in a standard parametric test of statistical significance such as Student's T-test, where p<0.05.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human patient, to provide a therapeutic benefit such as amelioration of symptoms, slowing of disease progression, or prevention of disease.

As used herein, "treatment" or "treating" refers to any treatment of a disease in a patient, including:
  a) preventing the disease, that is, causing the clinical symptoms of the disease not to develop;
  b) inhibiting the disease;
  c) slowing or arresting the development of clinical symptoms; and/or
  d) relieving the disease, that is, causing the regression of clinical symptoms.

As used herein, "patient" refers to an animal, such as a mammal, that has been or will be the object of treatment, observation or experiment. The methods described herein can be useful in both human therapy and veterinary applications. In some embodiments, the patient is a mammal; in some embodiments the patient is human; and in some embodiments the patient is chosen from cats and dogs.

Provided is at least one chemical entity chosen from compounds of Formula I

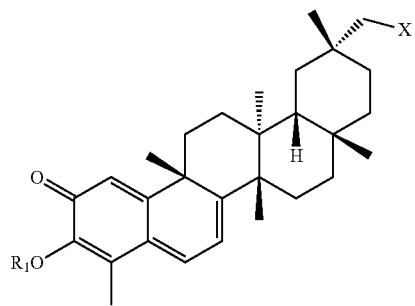

Formula I and pharmaceutically acceptable salts thereof, wherein
$R_1$ is chosen from hydrogen, optionally substituted alkyl, optionally substituted acyl, optionally substituted aminocarbonyl, optionally substituted alkoxycarbonyl, —P(=O)(OR$^a$)(OR$^b$), and —C(R$^c$)(R$^d$)OP(=O)(OR$^a$)(OR$^b$), where R$^a$, R$^b$, R$^c$, and R$^d$ are independently chosen from hydrogen, optionally substituted alkyl, optionally substituted cycloalkyl, optionally substituted heterocycloalkyl, optionally substituted aryl, and optionally substituted heteroaryl;

X is chose from —OR$_2$ and —NR$_3$R$_4$;

R$_2$ is chosen from hydrogen, optionally substituted alkyl, optionally substituted aryl, optionally substituted cycloalkyl, optionally substituted heteroaryl, optionally substituted heteroclycloalkyl, optionally substituted acyl, optionally substituted aminocarbonyl, and optionally substituted alkoxycarbonyl;

R$_3$ is chosen from hydrogen, optionally substituted alkyl, optionally substituted aryl, optionally substituted cycloalkyl, optionally substituted heteroaryl, optionally substituted heteroclycloalkyl, optionally substituted acyl, optionally substituted aminocarbonyl, optionally substituted alkoxycarbonyl, and optionally substituted sulfonyl; and R$_4$ is chosen from hydrogen, optionally substituted alkyl, optionally substituted aryl, optionally substituted cycloalkyl, optionally substituted heteroaryl, optionally substituted heteroclycloalkyl, optionally substituted alkoxy, optionally substituted cycloalkyloxy, and optionally substituted heterocycloalkyloxy;

or R$_3$ and R$_4$ may optionally be joined together with any intervening atoms to form an optionally substituted heterocycloalkyl ring provided that the compound of Formula I is not (6bS,8aS, 11R,12aR,12bS,14aR)-3-hydroxy-11-(hydroxymethyl)-4, 6b,8a,11,12b,14a-hexamethyl-7,8,8a,9,10,11,12,12a,12b, 13,14,14a-dodecahydropicen-2(6bH)-one.

In some embodiments, R$_1$ is chosen from hydrogen and optionally substituted alkyl. In some embodiments, R$_1$ is chosen from hydrogen and lower alkyl.

In some embodiments, R$_1$ is chosen from optionally substituted acyl. In some embodiments, R$_1$ is chosen from —COCH$_3$ and —COCH$_2$CH$_3$.

In some embodiments, R$_1$ is chosen from —P(=O)(OR$^a$)(OR$^b$), and —C(R$^c$)(R$^d$)OP(=O)(OR$^a$)(OR$^b$), where R$^a$, R$^b$, R$^c$, and R$^d$ are independently chosen from hydrogen, optionally substituted alkyl, optionally substituted cycloalkyl, optionally substituted heterocycloalkyl. In some embodiments, R$_1$ is chosen from —PO$_3$H$_2$. In some embodiments, R$_1$ is chosen from —CH$_2$OPO$_3$H$_2$.

In some embodiments, R$_2$ is chosen from optionally substituted aminocarbonyl. In some embodiments, R$_2$ is chosen from —CONH$_2$ and —CONHCH$_3$.

In some embodiments, R$_2$ is chosen from optionally substituted acyl and optionally substituted lower alkyl. In some embodiments, R$_2$ is acyl optionally substituted with amino. In some embodiments, R$_2$ is lower alkyl optionally substituted with amino.

In some embodiments, R$_3$ is chosen from hydrogen and optionally substituted lower alkyl. In some embodiments, R$_3$ is chosen from hydrogen and lower alkyl.

In some embodiments, R$_3$ is chosen from optionally substituted aminocarbonyl. In some embodiments, R$_3$ is —CONR$^b$R$^c$ where R$^b$ and R$^c$ are independently selected from hydrogen and lower alkyl. In some embodiments, R$_3$ is —CONR$^b$R$^c$, where R$^b$ and R$^c$ taken together with the nitrogen to which they are bound, form an optionally substituted 5- to 7-membered nitrogen-containing heterocycloalkyl which optionally includes 1 or 2 additional heteroatoms chosen from O, N, and S in the heterocycloalkyl ring. In some embodiments, R$_3$ is morpholine-4-carbonyl or piperazine-1-carbonyl, each of which is optionally substituted with lower alkyl.

In some embodiments, R$_3$ is chosen from optionally substituted alkoxycarbonyl. In some embodiments, R$_3$ is C$_1$-C$_6$ alkoxycarbonyl.

In some embodiments, R$_3$ is chosen from optionally substituted acyl. In some embodiments, R$_3$ is chosen from —COCH$_2$—NR$^b$R$^c$, where R$^b$ and R$^c$ are independently selected from hydrogen and lower alkyl.

In some embodiments, R$_3$ is chosen from optionally substituted sulfonyl.

In some embodiments, R$_4$ is chosen from hydrogen and optionally substituted lower alkyl. In some embodiments, R$_4$ is chosen from hydrogen and lower alkyl.

In some embodiments, R$_3$ and R$_4$ joined together with any intervening atoms form an optionally substituted 5- to 8-membered heterocycloalkyl ring. In some embodiments, R$_3$ and R$_4$ joined together with any intervening atoms form a heterocycloalkyl ring chosen from pyrrolidinyl, morpholinyl, and 2-oxopiperazine.

Also provided is at least one chemical entity chosen from
(6bS,8aS,11R,12aR,12bS,14aR)-11-(aminomethyl)-3-hydroxy-4,6b,8a,11,12b,14a-hexamethyl-7,8,8a,9,10,11,12, 12a,12b,13,14,14a-dodecahydropicen-2(6bH)-one;
((2R,4aS,6aS,12bR,14aS,14bR)-10-hydroxy-2,4-a,6a,9, 12b,14a-hexamethyl-11-oxo-1,2,3,4,4a,5,6,6a,11,12b,13, 14,14a,14b-tetradecahydropicen-2-yl)methyl methyl carbonate;
1-(((2R,4aS,6aS,12bR,14aS,14bR)-10-hydroxy-2,4-a,6a,9, 12b,14a-hexamethyl-11-oxo-1,2,3,4,4a,5,6,6a,11,12b,13, 14,14a,14b-tetradecahydropicen-2-yl)methyl)urea;
N-(((2R,4aS,6aS,12bR,14aS,14bR)-10-hydroxy-2,4-a,6a,9, 12b,14a-hexamethyl-11-oxo-1,2,3,4,4a,5,6,6a,11,12b,13, 14,14a,14b-tetradecahydropicen-2-yl)methyl)morpholine-4-carboxamide;
N-(((2R,4aS,6aS,12bR,14aS,14bR)-10-hydroxy-2,4-a,6a,9, 12b,14a-hexamethyl-11-oxo-1,2,3,4,4a,5,6,6a,11,12b,13, 14,14a,14b-tetradecahydropicen-2-yl)methyl)-4-methylpiperazine-1-carboxamide;
2-(dimethylamino)-N-(((2R,4aS,6aS,12bR,14aS,14bR)-10-hydroxy-2,4a,6a,9,12b,14a-hexamethyl-11-oxo-1,2,3,4, 4a,5,6,6a,11,12b,13,14,14a,14b-tetradecahydropicen-2-yl)methyl)acetamide;
(6bS,8aS,11R,12aR,12bS,14aR)-3-hydroxy-4,6b,8a,11,12b, 14a-hexamethyl-11-(morpholinomethyl)-7,8,8a,9,10,11, 12,12a,12b,13,14,14a-dodecahydropicen-2(6bH)-one;
(6bS,8aS,11R,12aR,12bS,14aR)-11-((dimethylamino)methyl)-3-hydroxy-4,6b,8a,11,12b,14a-hexamethyl-7,8,8a, 9,10,11,12,12a,12b,13,14,14a-dodecahydropicen-2 (6bH)-one;
(6bS,8aS,11R,12aR,12bS,14aR)-3-hydroxy-4,6b,8a,11,12b, 14a-hexamethyl-11-(pyrrolidin-1-yl methyl)-7,8,8a,9,10, 11,12,12a,12b,13,14,14a-dodecahydropicen-2(6bH)-one;
(6bS,8aS,11R,12aR,12bS,14aR)-3-hydroxy-4,6b,8a,11,12b, 14a-hexamethyl-11-(pyrrolidin-1-ylmethyl)-7,8,8a,9,10, 11,12,12a,12b,13,14,14a-dodecahydropicen-2(6bH)-one;
(6bS,8aS,11R,12aR,12bS,14aR)-3-hydroxy-11-((R)-3-hydroxypyrrolidin-1-yl)methyl)-4,6b,8a,11,12b,14a-hexamethyl-7,8,8a,9,10,11,12,12a,12b,13,14,14a-dodecahydropicen-2(6bH)-one;
(6bS,8aS,11R,12aR,12bS,14aR)-3-hydroxy-11-((S)-3-hydroxypyrrolidin-1-yl)methyl)-4,6b,8a,11,12b,14a-hexamethyl-7,8,8a,9,10,11,12,12a,12b,13,14,14a-dodecahydropicen-2(6bH)-one;
N-(((2R,4aS,6aS,12bR,14aS,14bR)-10-hydroxy-2,4-a,6a,9, 12b,14a-hexamethyl-11-oxo-1,2,3,4,4a,5,6,6a,11,12b,13, 14,14a,14b-tetradecahydropicen-2-yl)methyl)piperazine-1-carboxamide;
((2R,4aS,6aS,12bR,14aS,14bR)-10-hydroxy-2,4-a,6a,9, 12b,14a-hexamethyl-11-oxo-1,2,3,4,4a,5,6,6a,11,12b,13, 14,14a,14b-tetradecahydropicen-2-yl)methyl piperazine-1-carboxylate;

((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 4-methylpiperazine-1-carboxylate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl dimethylcarbamate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 2-(piperidin-1-yl)acetate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 2-morpholinoacetate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 2-(4-methylpiperazin-1-yl)acetate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 2-(dimethylamino)-3-methylbutanoate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 4-amino-2-(dimethylamino)-4-oxobutanoate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 2,4-diamino-4-oxobutanoate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methylpyrrolidine-2-carboxylate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl 2-(pyrrolidin-1-yl)acetate;
(6bS,8aS,11R,12aR,12bS,14aR)-3-hydroxy-4,6b,8a,11,12b,
   14a-hexamethyl-11-(piperazin-1-ylmethyl)-7,8,8a,9,10,
   11,12,12a,12b,13,14,14a-dodecahydropicen-2(6bH)-one;
(6bS,8aS,11R,12aR,12bS,14aR)-3-hydroxy-4,6b,8a,11,12b,
   14a-hexamethyl-11-((4-methylpiperazin-1-yl)methyl)-7,
   8,8a,9,10,11,12,12a,12b,13,14,14a-dodecahydropicen-2
   (6bH)-one;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl methylcarbamate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl dimethylcarbamate;
((2R,4aS,6aS,12bR,14aS,14bR)-10-hydroxy-2,4-a,6a,9,
   12b,14a-hexamethyl-11-oxo-1,2,3,4,4a,5,6,6a,11,12b,13,
   14,14a,14b-tetradecahydropicen-2-yl)methyl carbamate;
((2R,4aS,6aS,12bR,14aS,14bR)-2,4-a,6a,9,12b,14a-hexamethyl-11-oxo-10-(phosphonooxy)-1,2,3,4,4a,5,6,6a,11,
   12b,13,14,14a,14b-tetradecahydropicen-2-yl)methyl carbamate; and
(6bS,8aS,11R,12aR,12bS,14aR)-4,6b,8a,11,12b,14a-hexamethyl-2-oxo-11-(ureidomethyl)-2,6b,7,8,8a,9,10,11,
   12,12a,12b,13,14,14a-tetradecahydropicen-3-yl dihydrogen phosphate;
and pharmaceutically acceptable salts thereof.

Celastrol can be obtained from plants, e.g. *Tripterygium wilfordii* Hook, and is commercially available. Many of the optionally substituted starting compounds and other reactants are commercially available, e.g. from Aldrich Chemical Company (Milwaukee, Wis.) or can be readily prepared by those skilled in the art using commonly employed synthetic methodology.

The chemical entities described herein can be synthesized utilizing techniques well known in the art from commercially available starting materials and reagents.

The chemical entities described herein may be prepared in substantially pure form, typically by standard chromatographic methods, prior to formulation in a pharmaceutically acceptable form.

Chemical entities described herein having the desired pharmacological activity may be administered, in some embodiments, as a pharmaceutically acceptable composition comprising a pharmaceutical excipient, to a patient, as described herein. Depending upon the manner of introduction, the chemical entities may be formulated in a variety of ways as discussed below. The concentration of the at least one chemical entity in the formulation may vary from about 0.01-100 wt. %.

The administration of the chemical entities described herein can be done in a variety of ways, including, but not limited to, orally, subcutaneously, intravenously, intranasally, transdermally, intraperitoneally, intramuscularly, intrapulmonary, vaginally, rectally, or intraocularly.

Pharmaceutical dosage forms include at least one chemical entity described herein and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 21$^{st}$ Edition, Lippincott Williams & Wilkins (2005); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington: The Science and Practice of Pharmacy, Lippincott Williams & Wilkins (2005). The pH of such IV fluids may vary, and will typically be from 3.5 to 8 as known in the art.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

When a chemical entity described herein is administered into a human subject, the daily dosage will normally be determined by the prescribing physician with the dosage generally varying according to the age, weight, and response of the individual subject, as well as the severity of the subject's symptoms.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The chemical entities described herein may be administered concurrently (e.g., simultaneously, essentially simultaneously or within the same treatment protocol) or sequentially, depending upon the nature of the disease, the condition of the subject, and the actual choice of therapeutic agents to be administered in conjunction (i.e., within a single treatment protocol) with the chemical entity/composition.

EXAMPLES

The following examples serve to more fully describe the manner of using the invention. These examples are presented for illustrative purposes and should not serve to limit the true scope of the invention.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Example 1

Preparation of (6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one

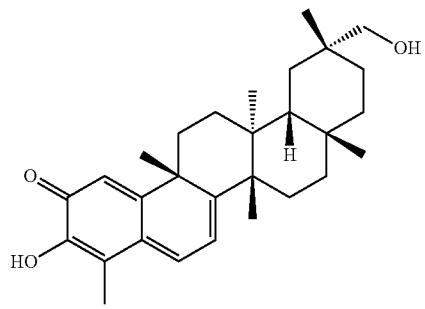

(6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one

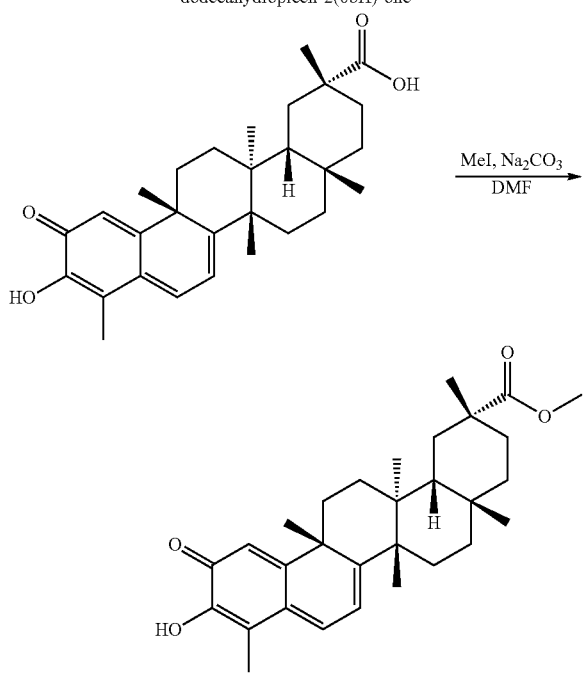

To a solution of celastrol (1.35 g, 3.0 mmol) in DMF (50 mL) were added $Na_2CO_3$ (0.636 g, 6.0 mmol. 2.0 eq) and MeI (0.469 g, 3.3 mmol, 1.1 eq). The mixture was stirred at rt overnight. The solvent was evaporated and the residue was purified by flash column chromatography (PE/EA=10/1, v/v) to afford (2R,4aS,6aS,12bR,14aS,14bR)-methyl 10-hydroxy-2,4-a,6a,9,12b,14a-hexamethyl-11-oxo-1,2,3,4,4a,5,6,6a,11,12b,13,14,14a,14b-tetradecahydropicene-2-carboxylate (1.25 g, 90%). LRMS (M+H$^+$) m/z calculated 464.64. found 465.2.

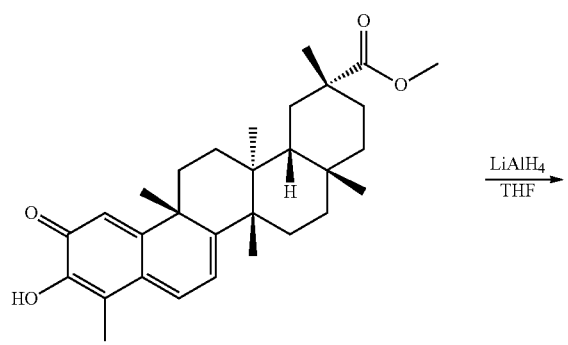

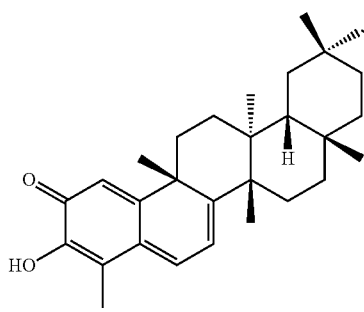

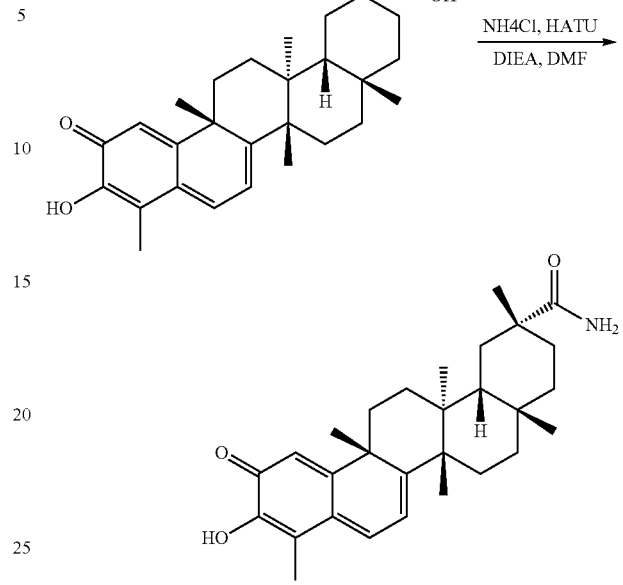

To a solution of (2R,4aS,6aS,12bR,14aS,14bR)-methyl 10-hydroxy-2,4-a,6a,9,12b,14a-hexamethyl-11-oxo-1,2,3,4,4a,5,6,6a,11,12b,13,14,14a,14b-tetradecahydropicene-2-carboxylate (215 mg, 0.46 mmol, 1 eq) in THF (25 mL) was added LiAlH$_4$ (35 mg, 0.93 mmol, 2.0 eq). The mixture was stirred at rt for 2 h, then quenched with H$_2$O and acidified with diluted HCl. The resulting mixture was extracted with EtOAc. The combined organic layers were dried over anhydrous Na$_2$SO$_4$ and concentrated. The resulting residue was purified via flash column chromatography (PE/EA=1/1, v/v) to afford (6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one as red solid (41 mg, 20%). LRMS (M+H$^+$) m/z calculated 436.63. found 437.3. $^1$H NMR (CDCl$_3$, 400 MHz) δ 6.96 (m, 2H), 6.46 (s, 1H), 6.30 (d, 1H), 3.36 (d, 1H), 3.14 (d, 1H), 2.14 (s, 3H), 2.03-2.06 (m, 1H), 1.49-1.85 (m, 12H), 1.37 (s, 3H), 1.23-1.27 (m, 1H), 1.25 (s, 3H),1.12 (s, 3H), 0.82-0.92 (m, 1H), 0.92 (s, 1H), 0.79-0.81 (m, 1H), 0.70 (s, 3H).

Example 2

Preparation of (6bS,8aS,11R,12aR,12bS,14aR)-11-(aminomethyl)-3-hydroxy-4,6b,8a,11,12b,14a-hexamethyl-7,8,8a,9,10,11,12,12a,12b,13,14,14a-dodecahydropicen-2(6bH)-one (6bS,8aS,11R,12aR,12bS,14aR)-11-(aminomethyl)-3-hydroxy-4,6b,8a,11,12b,14a-hexamethyl-7,8,8a,9,10,11,12,12a,12b,13,14,14a-dodecahydropicen-2(6bH)-one To a solution of celastrol (225 mg, 0.5 mmol, 1 eq) in DMF (15 mL) were added HATU (209 mg, 0.55 mmol. 1.1 eq), DIEA (129 mg, 1.0 mmol, 2.0 eq) and NH$_4$Cl (29 mg, 0.55 mmol, 1.1 eq). The mixture was stirred at rt overnight, and then was concentrated. The resulting residue was purified via flash column chromatography (PE/EA=1/1, v/v) to afford (2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicene-2-carboxamide (205 mg, 91%). LRMS (M+H$^+$) m/z calculated 449.29. found 450.3. $^1$H NMR (CDCl$_3$, 400 MHz) δ 7.00 (d, 2H), 6.51 (s, 1H), 6.32 (d, 1H), 5.62 (d, 2H), 2.42 (d, 1H), 2.21 (s, 3H), 2.15-1.83 (m, 7H), 1.70-1.46 (m, 6H), 1.43 (s, 3H), 1.28 (s, 3H), 1.20 (s, 3H), 1.12 (s, 3H), 1.03-0.86 (m, 1H), 0.72 (s, 3H).

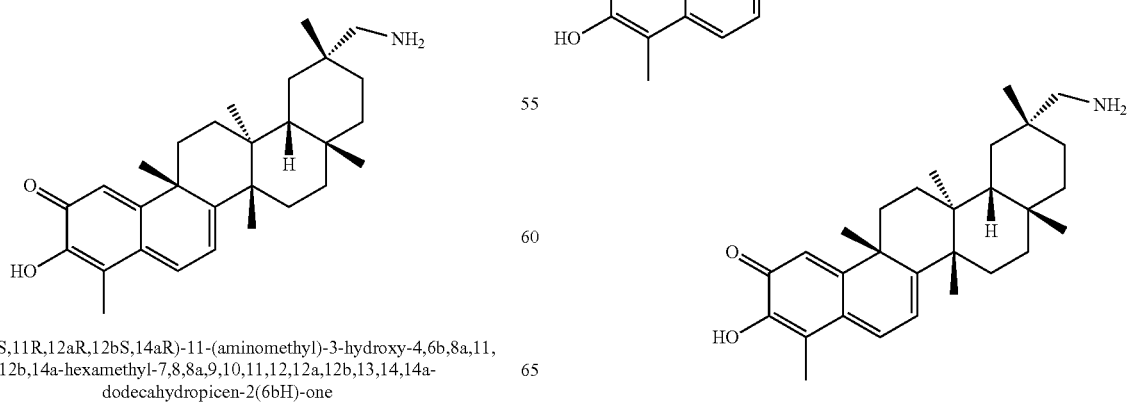

To a solution of (2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicene-2-carboxamide (33 mg, 0.07 mmol, 1 eq) in THF (10 mL) was added LiAlH₄ (39.9 mg, 1.05 mmol, 15 eq). The mixture was refluxed for 16 h, cooled to rt, quenched with H₂O, and acidified with diluted HCl. The resulting mixture was extracted with EtOAc. The organic layers were purified via preparative TLC (CH₂Cl₂/MeOH=10/1, v/v) to afford (6bS,8aS,11R,12aR,12bS,14aR)-11-(aminomethyl)-3-hydroxy-4,6b,8a,11,12b, 14a-hexamethyl-7,8,8a,9,10,11,12,12a,12b,13,14,14a-dodecahydropicen-2(6bH)-one as red solid (8 mg, 26.3%). LRMS (M+H⁺) m/z calculated 435.31. found 436.4. ¹H NMR (CD₃OD, 400 MHz) δ 7.29 (m, 1H), 6.52 (m, 1H), 6.51 (m, 1H), 2.96 (m, 1H), 2.85 (m, 1H), 2.27 (m, 4H), 2.20-1.50 (m, 14H), 1.34 (s, 9H), 1.20 (s, 3H), 0.89 (s, 3H).

Example 3

Preparation of N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide To a solution of (2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicene-2-carboxamide (701 mg, 1.56 mmol, 1 eq) in THF (50 mL) was added a solution of BH₃ in THF (1N, 7.8 mL, 5 eq) at 0° C. The resulting mixture was stirred at rt for 2 days, then quenched with water. The mixture was extracted with DCM (30 mL×3). The combined organic layers were dried over MgSO₄ and concentrated to give crude (6bR,8aS,11R,12aR,12bS,14aR)-11-(aminomethyl)-4,6b,8a,11,12b,14a-hexamethyl-6a,6b,7,8,8a,9,10,11,12,12a,12b,13,14,14a-tetradecahydropicene-2,3-diol (353 mg).

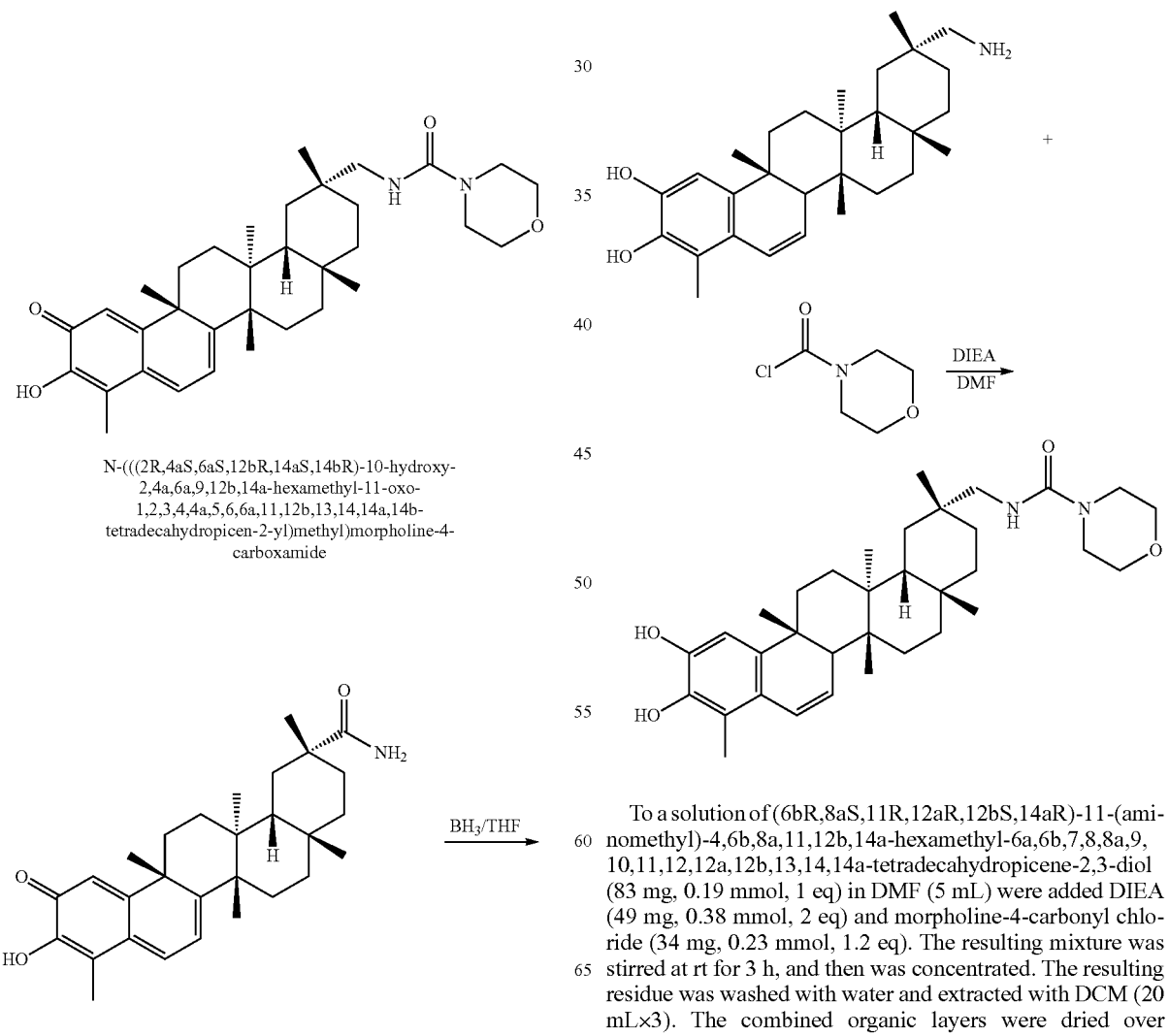

To a solution of (6bR,8aS,11R,12aR,12bS,14aR)-11-(aminomethyl)-4,6b,8a,11,12b,14a-hexamethyl-6a,6b,7,8,8a,9,10,11,12,12a,12b,13,14,14a-tetradecahydropicene-2,3-diol (83 mg, 0.19 mmol, 1 eq) in DMF (5 mL) were added DIEA (49 mg, 0.38 mmol, 2 eq) and morpholine-4-carbonyl chloride (34 mg, 0.23 mmol, 1.2 eq). The resulting mixture was stirred at rt for 3 h, and then was concentrated. The resulting residue was washed with water and extracted with DCM (20 mL×3). The combined organic layers were dried over MgSO₄, filtered and concentrated to give crude N-(((2R,4aS,6aR,12bR,14aS,14bR)-10,11-dihydroxy-2,4-a,6a,9,12b,14a-hexamethyl-1,2,3,4,4a,5,6,6a,6b,12b,13,14,14a,14b-tetradecahydropicen-2-yl)methyl)morpholine-4-carboxamide (65 mg).

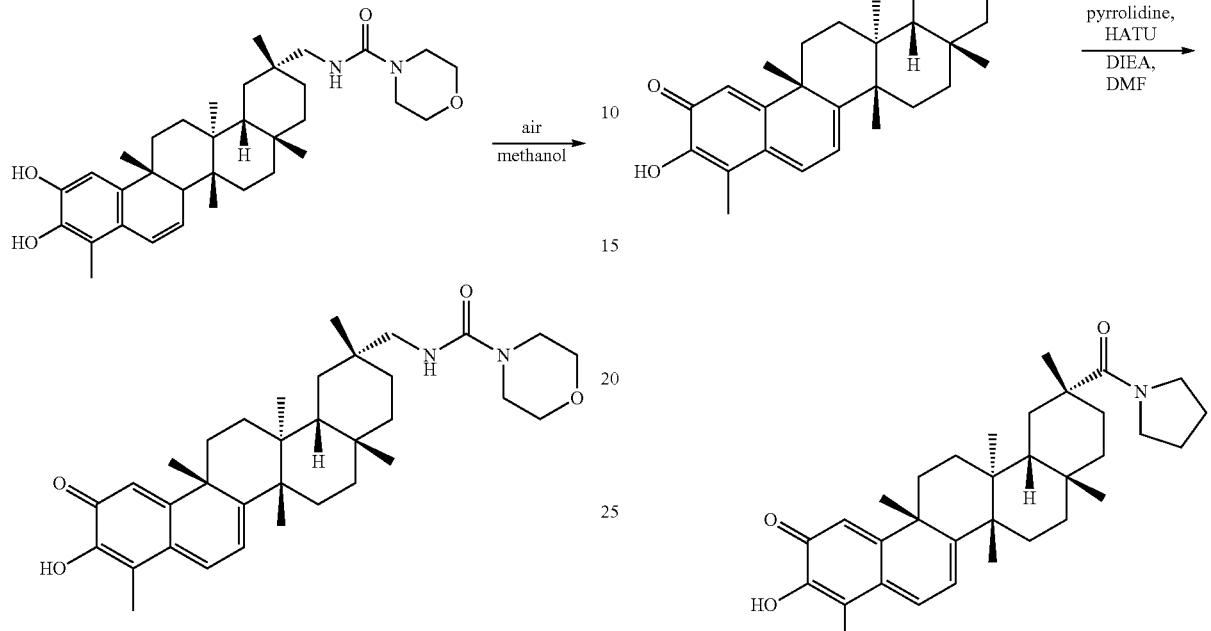

To a solution of crude N-(((2R,4aS,6aR,12bR,14aS,14bR)-10,11-dihydroxy-2,4-a,6a,9,12b,14a-hexamethyl-1,2,3,4,4a,5,6,6a,6b,12b,13,14,14a,14b-tetradecahydropicen-2-yl)methyl)morpholine-4-carboxamide (65 mg, 0.12 mmol) in methanol (30 mL) was bubbled with air overnight, then concentrated. The resulting residue was purified by flash column chromatography (PE/EA=1:1) and prep-HPLC to give N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide (3.7 mg). LRMS (M+H⁺) m/z calculated 548.36. found 549.5. ¹H NMR (CDCl₃, 400 MHz) δ7.03 (d, 1H), 6.96 (s, 1H), 6.51 (s, 1H), 6.38 (d, 1H), 4.44 (t, 1H), 3.69 (t, 4H), 3.33 (t, 4H), 3.33-3.37 (m, 1H), 2.90 (dd, 1H), 2.20 (s, 3H), 2.10-2.13 (m, 1H), 1.81-1.88 (m, 2H), 1.60-1.80 (m, 7H), 1.35-1.54 (m, 4H), 1.43 (s, 3H), 1.38 (s, 3H), 1.20 (s, 3H), 0.99 (s, 3H), 0.86-0.88 (m, 1H), 0.80 (s, 3H).

Example 4

Preparation of (6bS,8aS,11R,12aR,12bS,14aR)-3-hydroxy-4,6b,8a,11,12b,14a-hexamethyl-11-(pyrrolidin-1-ylmethyl)-7,8,8a,9,10,11,12,12a,12b,13,14,14a-dodecahydropicen-2(6bH)-one (6bS,8aS,11R,12aR,12bS,14aR)-3-hydroxy-4,6b,8a,11,12b,14a-hexamethyl-11-(pyrrolidin-1-ylmethyl)-7,8,8a,9,10,11,12,12a,12b,13,14,14a-dodecahydropicen-2(6bH)-one (6bS,8aS,11R,12aR,12bS,14aR)-3-hydroxy-4,6b,8a,11,12b,14a-Hexamethyl-11-(pyrrolidine-1-carbonyl)-7,8,8a,9,10,11,12,12a,12b,13,14,14a-dodecahydropicen-2(6bH)-one was prepared as described for (2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicene-2-carboxamide. LRMS (M+H⁺) m/z calculated 503.34. found 504.1. ¹H NMR (CDCl₃, 400 MHz) δ 7.03 (d, 1H), 6.98 (s, 1H), 6.53 (s, 1H), 6.43 (d, 1H), 3.65-3.61 (m, 2H), 3.46-3.42 (m, 1H), 3.26-3.22 (m, 1H), 2.42-2.35 (m, 2H), 2.22 (s, 3H), 2.19-2.05 (m, 2H), 1.92-1.52 (m, 10H), 1.46 (s, 3H), 1.33-1.27 (m, 5H), 1.26 (s, 3H), 1.22 (s, 3H), 1.09-0.95 (m, 1H), 0.90-0.83 (m, 2H), 0.55 (s, 3H).

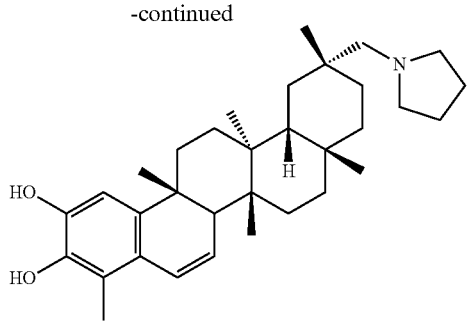

(6bR,8aS,11R,12aR,12bS,14aR)-4,6b,8a,11,12b,14a-Hexamethyl-11-(pyrrolidin-1-yl methyl)-6a,6b,7,8,8a,9,10,11,12,12a,12b,13,14,14a-tetradecahydropicene-2,3-diol was prepared as described for (6bR,8aS,11R,12aR,12bS,14aR)-11-(aminomethyl)-4,6b,8a,11,12b,14a-hexamethyl-6a,6b,7,8,8a,9,10,11,12,12a,12b,13,14,14a-tetradecahydropicene-2,3-diol.

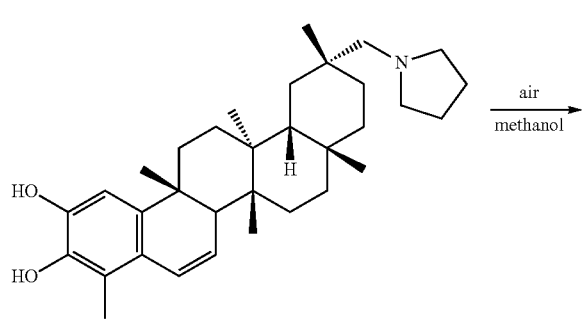

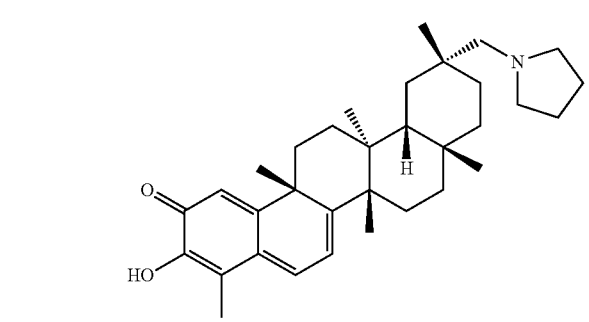

(6bS,8aS,11R,12aR,12bS,14aR)-3-hydroxy-4,6b,8a,11,12b,14a-Hexamethyl-11-(pyrrolidin-1-ylmethyl)-7,8,8a,9,10,11,12,12a,12b,13,14,14a-dodecahydropicen-2(6bH)-one was prepared as described for N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide. LRMS (M+H$^+$) m/z calculated 489.36. found 490.0. $^1$H NMR (CDCl$_3$, 400 MHz) δ7.03 (d, 1H), 6.53 (s, 1H), 6.38 (d, 1H), 2.50-2.65 (m, 4H), 2.34-2.37 (m, 1H), 2.10-2.20 (m, 2H), 2.17 (s, 3H), 1.55-1.89 (m, 13H), 1.35-1.45 (m, 3H), 1.44 (s, 3H), 1.39 (s, 3H), 1.21 (s, 3H), 1.05 (s, 3H), 0.86-0.97 (m, 1H), 0.80 (s, 3H).

Example 5

Preparation of (6bS,8aS,11R,12aR,12bS,14aR)-3-hydroxy-4,6b,8a,11,12b,14a-hexamethyl-11-(morpholinomethyl)-7,8,8a,9,10,11,12,12a,12b,13,14,14a-dodecahydropicen-2(6bH)-one

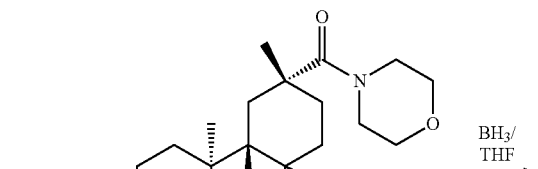

(6bS,8aS,11R,12aR,12bS,14aR)-3-hydroxy-4,6b,8a,11,12b,14a-hexamethyl-11-(morpholinomethyl)-7,8,8a,9,10,11,12,12a,12b,13,14,14a-dodecahydropicen-2(6bH)-one

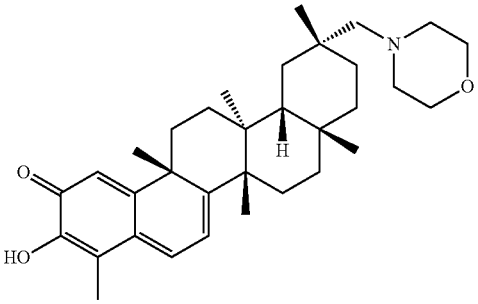

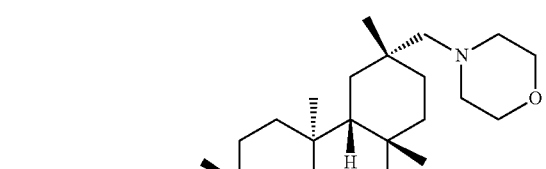

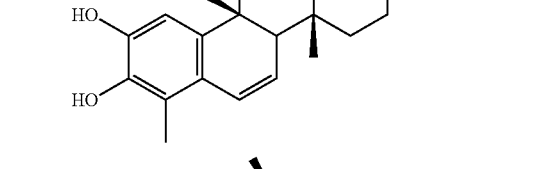

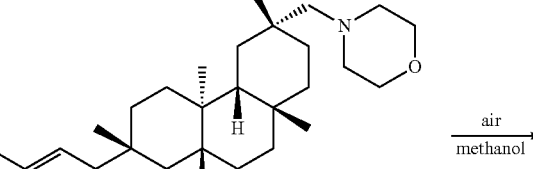

31
-continued

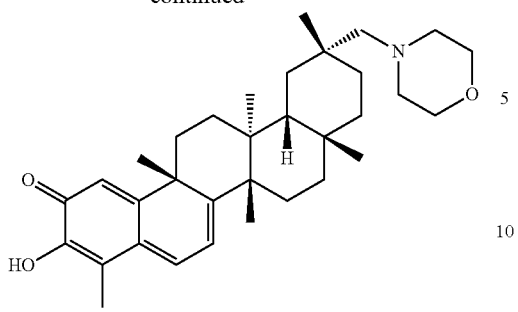

(6bS,8aS,11R,12aR,12bS,14aR)-3-hydroxy-4,6b,8a,11,
12b,14a-Hexamethyl-11-(morpholinomethyl)-7,8,8a,9,10,
11,12,12a,12b,13,14,14a-dodecahydropicen-2(6bH)-one
was prepared as described for N-(((2R,4aS,6aS,12bR,14aS,
14bR)-10-hydroxy-2,4-a,6a,9,12b,14a-hexamethyl-11-oxo-
1,2,3,4,4a,5,6,6a,11,12b,13,14,14a,14b-tetradecahydropicen-2-yl)methyl)morpholine-4-carboxamide. LRMS
(M+H$^+$) m/z calculated 505.36. found 506.1. $^1$H NMR
(CDCl$_3$, 400 MHz) δ7.04 (d, 1H), 6.97 (s, 1H), 6.53 (s, 1H),
6.38 (d, 1H), 3.66 (t, 1H), 2.49 (t, 4H), 2.20 (s, 3H), 2.00-2.22
(m, 3H), 1.50-1.88 (m, 9H), 1.33-1.50 (m, 4H), 1.41 (s, 3H),
1.35 (s, 3H), 1.21 (s, 3H), 1.01 (s, 3H), 0.88-0.99 (m, 1H),
0.79 (s, 3H).

Example 6

Preparation of (6bS,8aS,11R,12aR,12bS,14aR)-11-
((dimethylamino)methyl)-3-hydroxy-4,6b,8a,11,12b,
14a-hexamethyl-7,8,8a,9,10,11,12,12a,12b,13,14,
14a-dodecahydropicen-2(6bH)-one

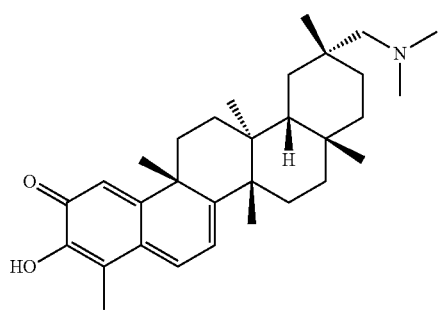

(6bS,8aS,11R,12aR,12bS,14aR)-11-(dimethlyamino)methyl)-3-hydroxy-
4,6b,8a,11,12b,14a-hexamethyl-7,8,8a,9,10,11,12,12a,12b,13,14,14a-
dodecahydropicen-2(6bH)-one

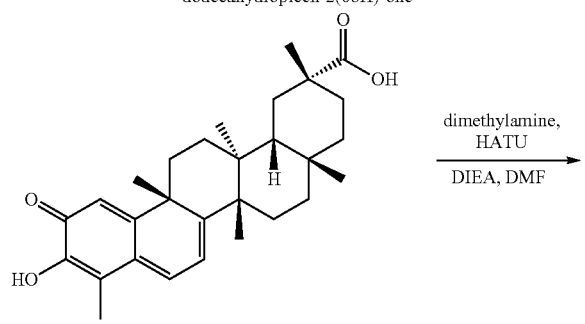

dimethylamine,
HATU
⎯⎯⎯⎯⎯→
DIEA, DMF

32
-continued

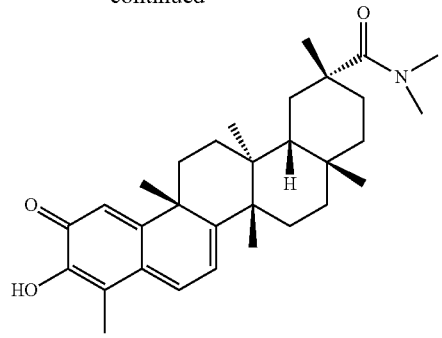

(2R,4aS,6aS,12bR,14aS,14bR)-10-hydroxy-N,N,2,4a,6a,
9,12b,14a-octamethyl-11-oxo-1,2,3,4,4a,5,6,6a,11,12b,13,
14,14a,14b-tetradecahydropicene-2-carboxamide was prepared as described for (2R,4aS,6aS,12bR,14aS,14bR)-10-
hydroxy-2,4-a,6a,9,12b,14a-hexamethyl-11-oxo-1,2,3,4,4a,
5,6,6a,11,12b,13,14,14a,14b-tetradecahydropicene-2-
carboxamide. LRMS (M+H$^+$) m/z calculated 477.32. found
478.1. $^1$H NMR (CDCl$_3$, 400 MHz) δ 7.03 (d, 1H), 6.97 (s,
1H), 6.53 (s, 1H), 6.36 (d, 1H), 3.04 (s, 3H), 2.83 (s, 3H),
2.44-2.33 (m, 2H), 2.22 (s, 3H), 2.22-2.08 (m, 2H), 1.89-1.49
(m, 7H), 1.46 (s, 3H), 1.35-1.25 (m, 8H), 1.14 (s, 3H), 1.00-
0.96 (m, 1H), 0.88-0.85 (m, 1H), 0.54 (s, 3H).

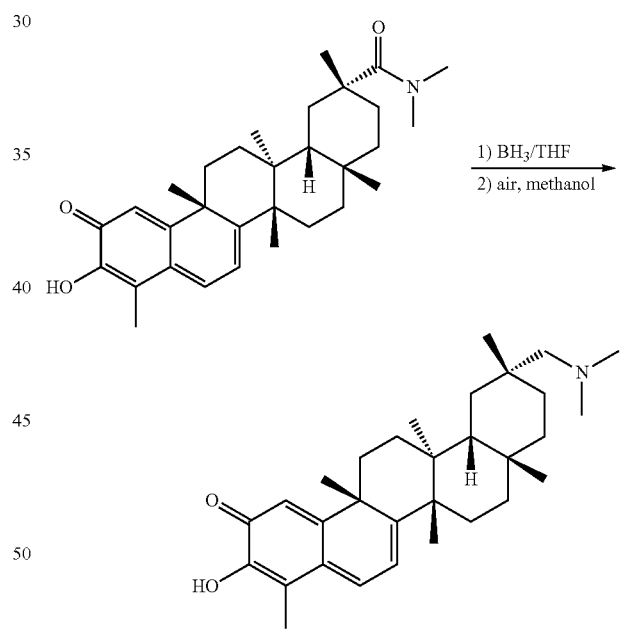

1) BH$_3$/THF
2) air, methanol (6bS,8aS,11R,12aR,12bS,14aR)-11-((Dimethylamino)
methyl)-3-hydroxy-4,6b,8a,11,12b,14a-hexamethyl-7,8,8a,
9,10,11,12,12a,12b,13,14,14a-dodecahydropicen-2(6bH)-
one was reduced as described for (6bR,8aS,11R,12aR,12bS,
14aR)-11-(aminomethyl)-4,6b,8a,11,12b,14a-hexamethyl-
6a,6b,7,8,8a,9,10,11,12,12a,12b,13,14,14a-
tetradecahydropicene-2,3-diol and then oxidized as
described for N-(((2R,4aS,6aS,12bR,14aS,14bR)-10-hydroxy-2,4-a,6a,9,12b,14a-hexamethyl-11-oxo-1,2,3,4,4a,5,
6,6a,11,12b,13,14,14a,14b-tetradecahydropicen-2-yl)methyl)morpholine-4-carboxamide. LRMS (M+H$^+$) m/z
calculated 463.35. found 464.2. $^1$H NMR (CDCl$_3$, 400 MHz)
δ 7.03 (d, 1H), 6.52 (s, 1H), 6.39 (d, 1H), 2.32 (s, 6H), 2.22 (s, 3H), 2.22-2.18 (m, 1H), 2.11-2.05 (m, 3H), 1.91-1.62 (m, 9H), 1.53-1.35 (m, 9H), 1.23 (s, 3H), 1.07 (s, 3H), 1.01-0.97 (m, 1H), 0.79 (s, 3H).

Example 7

Preparation of N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)-4-methylpiperazine-1-carboxamide

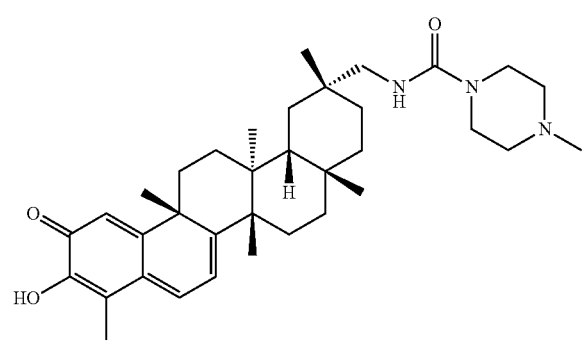

N-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)-4-methylpiperazine-1-carboxamide

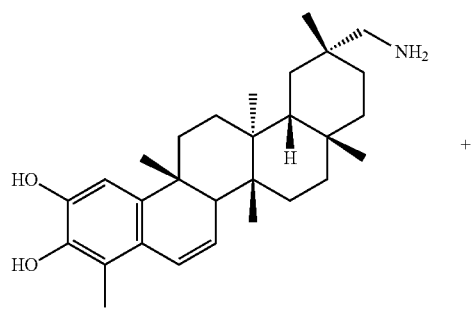

+

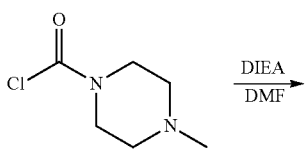

$\xrightarrow{\text{DIEA}}{\text{DMF}}$

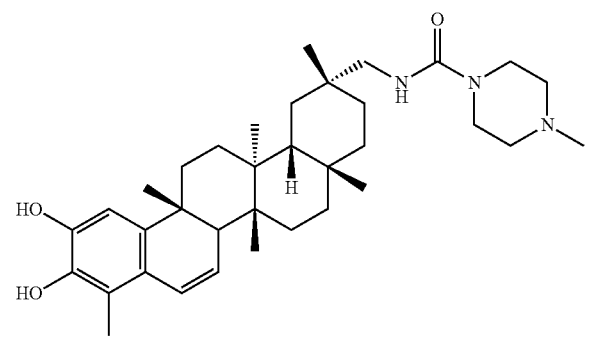

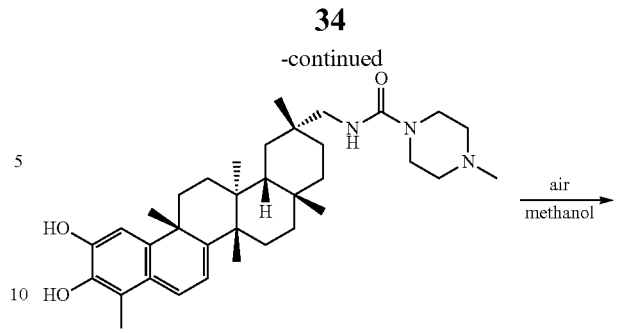

$\xrightarrow[\text{methanol}]{\text{air}}$

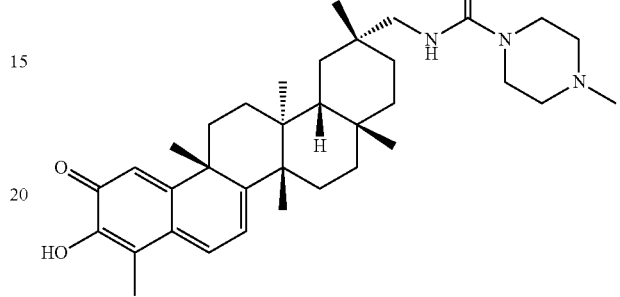

N-(((2R,4aS,6aS,12bR,14aS,14bR)-10-hydroxy-2,4-a,6a,9,12b,14a-Hexamethyl-11-oxo-1,2,3,4,4a,5,6,6a,11,12b,13,14,14a,14b-tetradecahydropicen-2-yl)methyl)-4-methyl piperazine-1-carboxamide was prepared as described for N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide. LRMS (M+H$^+$) m/z calculated 561.39. found 562.0. $^1$H NMR (CDCl$_3$, 400 MHz) δ 7.03 (d, 1H), 6.51 (s, 1H), 6.38 (d, 1H), 4.46 (t, 1H), 3.36-3.43 (m, 4H), 3.28-3.32 (m, 1H), 2.89-2.94 (m, 1H), 2.41 (t, 4H), 2.32 (s, 3H), 2.22 (s, 3H), 2.10-2.13 (m, 1H), 2.00-2.05 (m, 1H), 1.83-1.90 (m, 3H), 1.60-1.80 (m, 6H), 1.30-1.47 (m, 4H), 1.42 (s, 3H), 1.33 (s, 3H), 1.20 (s, 3H), 0.98 (s, 3H), 0.80 (s, 3H).

Example 8

Preparation of 1-(((2R,4aS,6aS,12bR,14aS,14bR)-10-hydroxy-2,4-a,6a,9,12b,14a-hexamethyl-11-oxo-1,2,3,4,4a, 5,6,6a,11,12b,13,14,14a,14b-tetradecahydropicen-2-yl)methyl)urea

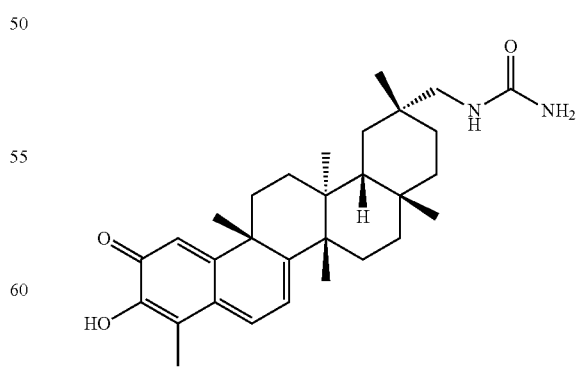

1-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)urea

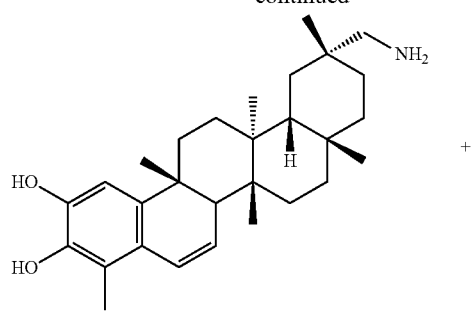

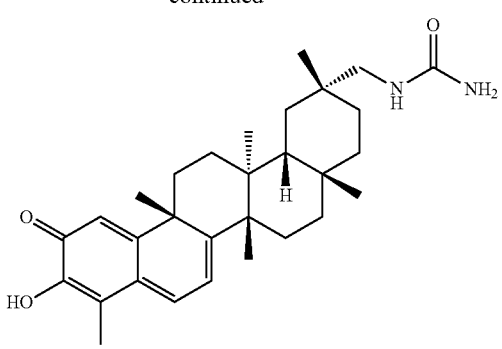

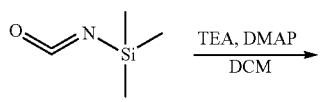

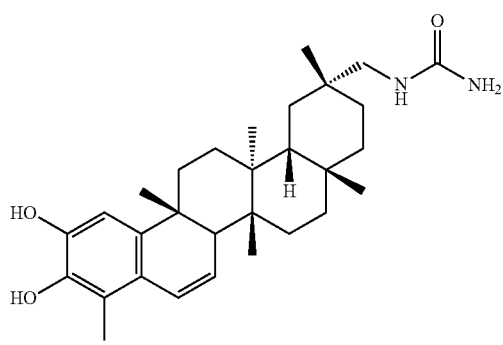

To a solution of (6bR,8aS,11R,12aR,12bS,14aR)-11-(aminomethyl)-4,6b,8a,11,12b,14a-hexamethyl-6a,6b,7,8,8a,9,10,11,12,12a,12b,13,14,14a-tetradecahydropicene-2,3-diol (51 mg, 0.12 mmol) in DCM (10 mL) were added TEA (24 mg, 0.24 mmol, 2.0 eq), DMAP (59 mg, 0.48 mmol, 4 eq) and trimethylsilyl isocyanate (16 mg, 0.14 mmol, 1.2 eq). The resulting mixture was stirred at rt overnight, and then saturated NH4Cl was added. The water phase was extracted with DCM (30 mL×3). The combined organic layers were dried over MgSO4, filtered and concentrated to give crude 1-(((2R,4aS,6aR,12bR,14aS,14bR)-10,11-dihydroxy-2,4-a,6a,9,12b,14a-hexamethyl-1,2,3,4,4a,5,6,6a,6b,12b,13,14,14a,14b-tetradecahydropicen-2-yl)methyl)urea (33 mg).

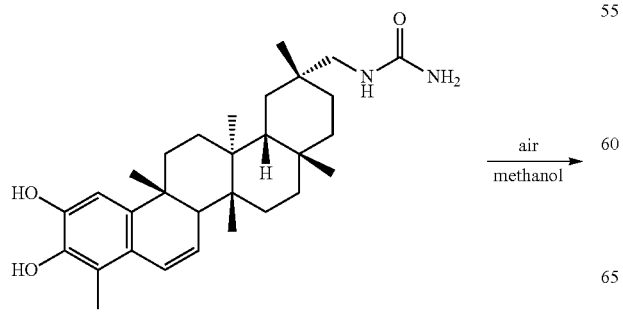

1-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)urea was prepared as described for N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide. LRMS (M+H$^+$) m/z calculated 478.32. found 478.8. $^1$H NMR (CDCl$_3$, 400 MHz) δ 7.03 (d, 1H), 7.00 (brs, 1H), 6.51 (s, 1H), 6.37 (d, 1H), 4.98 (brs, 1H), 4.58 (brs, 2H), 3.08-3.11 (m, 1H), 2.92-2.94 (m, 1H), 2.22 (s, 3H), 2.08-2.12 (m, 1H), 1.54-1.82 (m, 8H), 1.35-1.50 (m, 4H), 1.43 (s, 3H), 1.37 (s, 3H), 1.15-1.22 (m, 1H), 1.19 (s, 3H), 0.95-1.02 (m, 1H), 0.98 (s, 3H), 0.74 (s, 3H).

Example 9

Preparation of 2-(dimethylamino)-N-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)acetamide

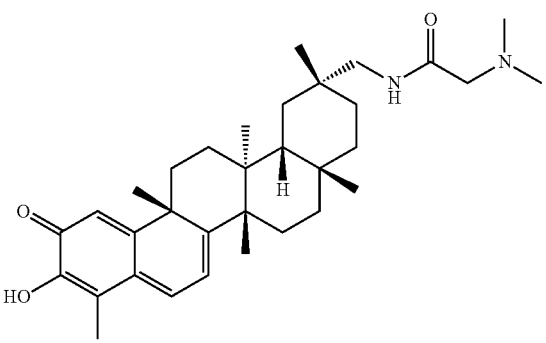

2-(dimethylamino)-N-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)acetamide -continued

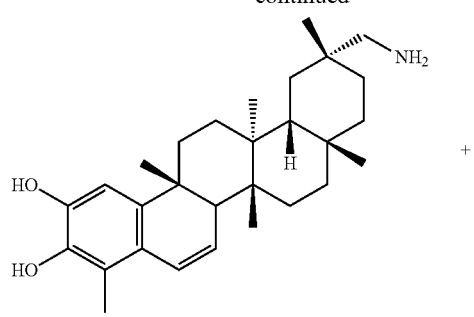

+

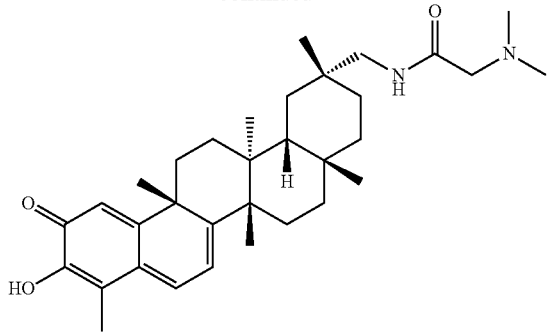

2-(dimethylamino)-N-(((2R,4aS,6aS,12bR,14aS,14bR)-10-Hydroxy-2,4-a,6a,9,12b, 14a-hexamethyl-11-oxo-1,2,3,4,4a,5,6,6a,11,12b,13,14,14a,14b-tetradecahydropicen-2-yl)methyl)acetamide was prepared as described for N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide. LRMS (M+H⁺) m/z calculated 520.37. found 521.1. $^1$H NMR (CDCl$_3$, 400 MHz) δ 7.36 (brs, 1H), 7.02 (d, 1H), 6.51 (s, 1H), 6.38 (d, 1H), 3.25-3.30 (m, 1H), 2.97-3.00 (m, 3H), 2.33 (s, 6H), 2.22 (s, 3H), 2.10-2.14 (m, 1H), 1.61-1.90 (m, 9H), 1.33-1.51 (m, 4H), 1.44 (s, 3H), 1.38 (s, 3H), 1.21 (s, 3H), 1.00-1.16 (m, 1H), 1.03 (s, 3H), 0.79 (s, 3H).

Example 10

Preparation of ((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl methyl carbonate

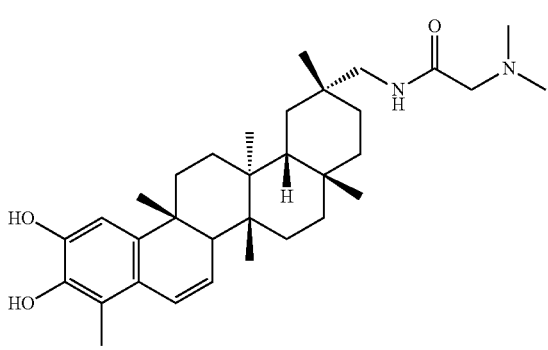

To a solution of N,N-dimethyl-glycine hydrochloride (48 mg, 0.34 mmol) in DMF (10 mL) were added HATU (155 mg, 0.41 mmol. 1.2 eq) and DIEA (88 mg, 0.68 mmol, 2.0 eq). The mixture was stirred at rt for 30 min, and then crude (6bR,8aS,11R,12aR,12bS,14aR)-11-(aminomethyl)-4,6b,8a,11,12b,14a-hexamethyl-6a,6b,7,8,8a,9,10,11,12,12a,12b,13,14,14a-tetradecahydropicene-2,3-diol (150 mg, 0.34 mmol, 1 eq) was added. The resulting mixture was stirred at rt overnight, and concentrated. The resulting residue was purified via flash column chromatography (PE/EA=1/1, v/v) to afford crude N-(((2R,4aS,6aR,12bR,14aS,14bR)-10,11-dihydroxy-2,4-a,6a,9,12b,14a-hexamethyl-1,2,3,4,4a,5,6,6a,6b,12b,13,14,14a,14b-tetradecahydropicen-2-yl)methyl)-2-(dimethylamino)acetamide (85 mg).

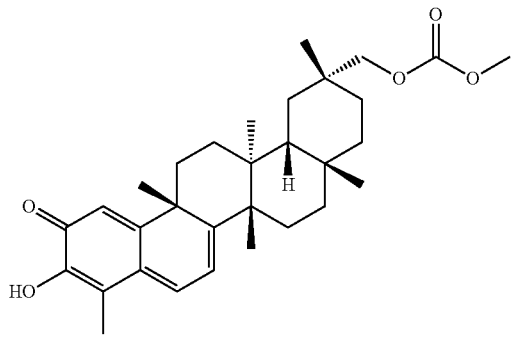

((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl methyl carbonate

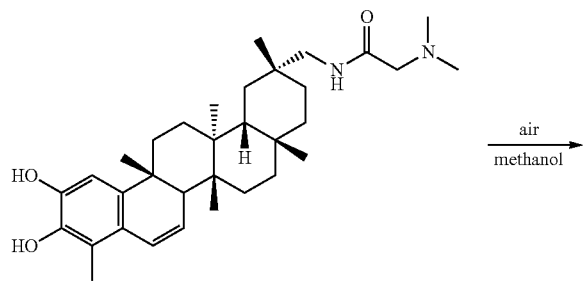

air
methanol
→

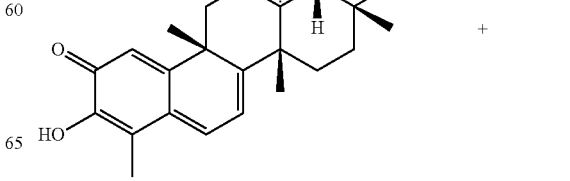

+

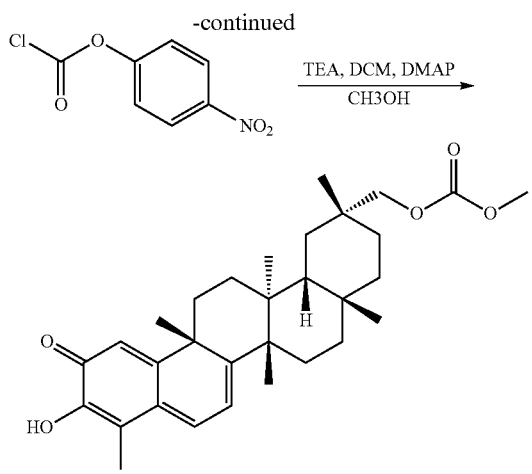

To a solution of (6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one (43.7 mg, 0.1 mmol) in DCM (50 mL) were added 4-nitrophenyl chloroformate (40.2 mg, 0.2 mmol. 2.0 eq) and TEA (25.2 mg, 0.25 mmol, 2.5 eq) and catalytic amount of DMAP at rt. The mixture was stirred for 1 h and methanol (1 mL) was added. The mixture was concentrated and the resulting residue was purified via preparative TLC (PE/EA=10/1, v/v) to afford ((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl methyl carbonate (4.1 mg).

LRMS (M+H$^+$) m/z calculated 494.30. found 495.1.

$^1$H NMR (CDCl$_3$, 400 MHz) δ 7.01-7.03 (d, 1H), 6.96 (s, 1H), 6.53 (s, 1H), 6.36-6.38 (d, 1H), 3.86-3.88 (t, 2H), 3.77 (s, 3H), 2.21 (s, 3H), 2.03-2.06 (m, 1H), 1.49-1.85 (m, 11H), 1.47 (s, 3H), 1.37 (s, 3H), 1.23-1.27 (m, 1H), 1.25 (m, 4H), 0.82-0.92 (m, 1H), 0.74 (s, 3H).

Example 11

Inhibition of Cell Growth in Tumor Cells

Inhibition of cell growth by compounds was measured using MTT assay (Mosmann, T., Journal of Immunological Methods, 1983, 65, 55-63). Tumor cell lines were purchased from ATCC (American Type Culture Collection, Manassas, Va.). All cell lines were maintained in RPMI 1640 (Hyclone) supplemented with 10% fetal bovine serum (FBS, Hyclone), glutamine (2 mM, Hyclone), and antibiotics (penicillin 100 U/mL and streptomycin 50 μg/mL) at 37° C. in a humidified atmosphere of 5% $CO_2$ in air. Taxol (positive control, Sigma) and compounds were dissolved in DMSO (Sigma), and the final concentration of DMSO in the medium was 1%. Tumor cells were plated in 96-well plates at densities from 4000 cells/well of a 96-well plate and allowed to adhere/grow for 24 h. They were then treated with various concentrations of drug for 72 h. 3-(4,5-Dimethylthiazol-2-yl)-2,5-diphenyltetrazolium bromide (MTT, Sigma) was used to determine the number of viable cells at the time of compound addition and the number of cells remaining after 72 h compound exposure. The number of cells remaining after 72 h was compared to the number of viable cells at the time of compound addition by measuring the absorbance at 570 nm, allowing for the calculation of growth inhibition.

All concentrations of compounds were tested in triplicate and controls were averaged over 4 wells. $IC_{50}$ was calculated by plotting the concentration of compound vs the percentage of inhibition in treated wells using GraphPad Prism 5. Data for representative compounds are shown below.

TABLE I

Inhibitory activity of representative compounds in A549 cells.

| Chemical Name | A549 cell $IC_{50}$ (nM) |
| --- | --- |
| (6bS,8aS,11R,12aR,12bS,14aR)-11-(aminomethyl)-3-hydroxy-4,6b,8a,11,12b,14a-hexamethyl-7,8,8a,9,10,11,12,12a,12b,13,14,14a-dodecahydropicen-2(6bH)-one | 841 |
| (6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one | 624 |
| ((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl methyl carbonate | 393 |
| 1-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)urea | 737 |
| N-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)morpholine-4-carboxamide | 358 |
| N-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)-4-methylpiperazine-1-carboxamide | 246 |
| 2-(dimethylamino)-N-(((2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicen-2-yl)methyl)acetamide | 159 |
| (6bS,8aS,11R,12aR,12bS,14aR)-3-hydroxy-4,6b,8a,11,12b,14a-hexamethyl-11-(morpholinomethyl)-7,8,8a,9,10,11,12,12a,12b,13,14,14a-dodecahydropicen-2(6bH)-one | 523 |

TABLE I-continued

Inhibitory activity of representative compounds in A549 cells.

| Chemical Name | A549 cell IC$_{50}$ (nM) |
|---|---|
| (6bS,8aS,11R,12aR,12bS,14aR)-11-((dimethylamino)methyl)-3-hydroxy-4,6b,8a,11,12b,14a-hexamethyl-7,8,8a,9,10,11,12,12a,12b,13,14,14a-dodecahydropicen-2(6bH)-one | 285 |
| (6bS,8aS,11R,12aR,12bS,14aR)-3-hydroxy-4,6b,8a,11,12b,14a-hexamethyl-11-(pyrrolidin-1-ylmethyl)-7,8,8a,9,10,11,12,12a,12b,13,14,14a-dodecahydropicen-2(6bH)-one | 498 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. At least one chemical entity chosen from compounds of Formula I

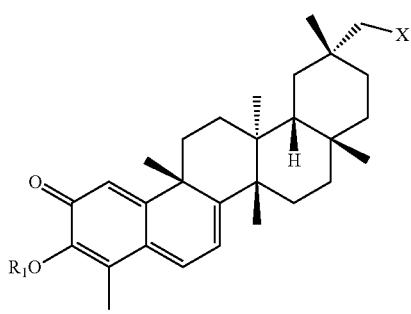

Formula I and pharmaceutically acceptable salts thereof, wherein
R$_1$ is chosen from hydrogen, optionally substituted alkyl, optionally substituted acyl, optionally substituted aminocarbonyl, optionally substituted alkoxycarbonyl, —P(=O)(OR$^a$)(OR$^b$), and —C(R$^c$)(R$^d$)OP(=O)(OR$^a$)(OR$^b$), where R$^a$, R$^b$, R$^c$, and R$^d$ are independently chosen from hydrogen, optionally substituted alkyl, optionally substituted cycloalkyl, optionally substituted heterocycloalkyl, optionally substituted aryl, and optionally substituted heteroaryl;
X is chose from –OR$_2$ and —NR$_3$R$_4$;
R$_2$ is chosen from hydrogen, optionally substituted alkyl, optionally substituted aryl, optionally substituted cycloalkyl, optionally substituted heteroaryl, optionally substituted heteroclycloalkyl, optionally substituted acyl, optionally substituted aminocarbonyl, and optionally substituted alkoxycarbonyl;
R$_3$ is chosen from hydrogen, optionally substituted alkyl, optionally substituted aryl, optionally substituted cycloalkyl, optionally substituted heteroaryl, optionally substituted heteroclycloalkyl, optionally substituted acyl, optionally substituted aminocarbonyl, optionally substituted alkoxycarbonyl, and optionally substituted sulfonyl; and
R$_4$ is chosen from hydrogen, optionally substituted alkyl, optionally substituted aryl, optionally substituted cycloalkyl, optionally substituted heteroaryl, optionally substituted heteroclycloalkyl, optionally substituted alkoxy, optionally substituted cycloalkyloxy, and optionally substituted heterocycloalkyloxy;
or R$_3$ and R$_4$ may optionally be joined together with any intervening atoms to form an optionally substituted heterocycloalkyl ring
provided that the compound of Formula I is not (6bS,8aS,11R,12aR,12bS,14aR)-3-hydroxy-11-(hydroxymethyl)-4,6b,8a,11,12b,14a-hexamethyl-7,8,8a,9,10,11,12,12a,12b,13,14,14a-dodecahydropicen-2(6bH)-one.

2. At least one chemical entity of claim 1 wherein R$_1$ is chosen from hydrogen and optionally substituted alkyl.

3. At least one chemical entity of claim 2 wherein R$_1$ is chosen from hydrogen and lower alkyl.

4. At least one chemical entity of claim 1 wherein R$_1$ is chosen from optionally substituted acyl.

5. At least one chemical entity of claim 4 wherein R$_1$ is chosen from —COCH$_3$ and —COCH$_2$CH$_3$.

6. At least one chemical entity of claim 1 wherein R$_1$ is chosen from —P(=O)(OR$^a$)(OR$^b$), and —C(R$^c$)(R$^d$)OP(=O)(OR$^a$)(OR$^b$), where R$^a$, R$^b$, R$^c$, and R$^d$ are independently chosen from hydrogen, optionally substituted alkyl, optionally substituted cycloalkyl, optionally substituted heterocycloalkyl.

7. At least one chemical entity of claim 6 wherein R$_1$ is chosen from —PO$_3$H$_2$.

8. At least one chemical entity of claim 6 wherein R$_1$ is chosen from —CH$_2$OPO$_3$H$_2$.

9. At least one chemical entity of claim 1 wherein R$_2$ is chosen from optionally substituted aminocarbonyl.

10. At least one chemical entity of claim 9 wherein R$_2$ is chosen from —CONH$_2$ and —CONHCH$_3$.

11. At least one chemical entity of claim 1 wherein R$_2$ is chosen from optionally substituted acyl and optionally substituted lower alkyl.

12. At least one chemical entity of claim 1 wherein R$_3$ is chosen from hydrogen and optionally substituted lower alkyl.

13. At least one chemical entity of claim 1 wherein R$_3$ is chosen from optionally substituted aminocarbonyl.

14. At least one chemical entity of claim 1 wherein R$_3$ is chosen from optionally substituted alkoxycarbonyl.

15. At least one chemical entity of claim 1 wherein R$_3$ is chosen from optionally substituted sulfonyl.

16. At least one chemical entity of claim 1 wherein R$_4$ is chosen from hydrogen and optionally substituted lower alkyl.

17. At least one chemical entity of claim 1 wherein R$_3$ and R$_4$ are joined together with any intervening atoms to form an optionally substituted 5- to 8-membered heterocycloalkyl ring.

18. At least one chemical entity chosen from compounds
(6bS,8aS,11R,12aR,12bS,14aR)-11-(aminomethyl)-3-hydroxy-4,6b,8a,11,12b,14a-hexamethyl-7,8,8a,9,10,11,12,12a,12b,13,14,14a-dodecahydropicen-2(6bH)-one;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl methyl carbonate;
1-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl) urea;
N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl) morpholine-4-carboxamide;
N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)-4-methyl piperazine-1-carboxamide;
2-(dimethylamino)-N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl)acetamide;
(6bS,8aS,11R,12aR,12bS,14aR)-3-hydroxy-4,6b,8a,11,12b,14a-hexamethyl-11-(morpholinomethyl)-7,8,8a,9,10,11,12,12a,12b,13,14,14a-dodecahydropicen-2(6bH)-one;
(6bS,8aS,11R,12aR,12bS,14aR)-11-((dimethylamino)methyl)-3-hydroxy-4,6b,8a,11,12b,14a-hexamethyl-7,8,8a,9,10,11,12,12a,12b,13,14,14a-dodecahydropicen-2(6bH)-one;
(6bS,8aS,11R,12aR,12bS,14aR)-3-hydroxy-4,6b,8a,11,12b,14a-hexamethyl-11-(pyrrolidin-1-ylmethyl)-7,8,8a,9,10,11,12,12a,12b,13,14,14a-dodecahydropicen-2(6bH)-one;
(6bS,8aS,11R,12aR,12bS,14aR)-3-hydroxy-4,6b,8a,11,12b,14a-hexamethyl-11-(pyrrolidin-1-ylmethyl)-7,8,8a,9,10,11,12,12a,12b,13,14,14a-dodecahydropicen-2(6bH)-one;
(6bS,8aS,11R,12aR,12bS,14aR)-3-hydroxy-11-(((R)-3-hydroxypyrrolidin-1-yl)methyl)-4,6b,8a,11,12b,14a-hexamethyl-7,8,8a,9,10,11,12,12a,12b,13,14,14a-dodecahydropicen-2(6bH)-one;
(6bS,8aS,11R,12aR,12bS,14aR)-3-hydroxy-11-(((S)-3-hydroxypyrrolidin-1-yl)methyl)-4,6b,8a,11,12b,14a-hexamethyl-7,8,8a,9,10,11,12,12a,12b,13,14,14a-dodecahydropicen-2(6bH)-one;
N-(((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl) piperazine-1-carboxamide;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl piperazine-1-carboxylate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 4-methylpiperazine-1-carboxylate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl dimethylcarbamate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 2-(piperidin-1-yl)acetate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 2-morpholinoacetate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 2-(4-methylpiperazin-1-yl)acetate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 2-(dimethylamino)-3-methylbutanoate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 4-amino-2-(dimethylamino)-4-oxobutanoate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 2,4-diamino-4-oxobutanoate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl pyrrolidine-2-carboxylate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl 2-(pyrrolidin-1-yl)acetate;
(6bS,8aS,11R,12aR,12bS,14aR)-3-hydroxy-4,6b,8a,11,12b,14a-hexamethyl-11-(piperazin-1-ylmethyl)-7,8,8a,9,10,11,12,12a,12b,13,14,14a-dodecahydropicen-2(6bH)-one;
(6bS,8aS,11R,12aR,12bS,14aR)-3-hydroxy-4,6b,8a,11,12b,14a-hexamethyl-11-((4-methylpiperazin-1-yl)methyl)-7,8,8a,9,10,11,12,12a,12b,13,14,14a-dodecahydropicen-2(6bH)-one;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl methylcarbamate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl dimethylcarbamate;
((2R,4aS,6aS,12bR,14aS,14bR)-10-hydroxy-2,4-a,6a,9,12b,14a-hexamethyl-11-oxo-1,2,3,4,4a,5,6,6a,11,12b,13,14,14a,14b-tetradecahydropicen-2-yl)methyl carbamate;
((2R,4aS,6aS,12bR,14aS,14bR)-2,4-a,6a,9,12b,14a-hexamethyl-11-oxo-10-(phosphonooxy)-1,2,3,4,4a,5,6,6a,11,12b,13,14,14a,14b-tetradecahydropicen-2-yl)methyl carbamate; and
(6bS,8aS,11R,12aR,12bS,14aR)-4,6b,8a,11,12b,14a-hexamethyl-2-oxo-11-(ureidomethyl)-2,6b,7,8,8a,9,10,11,12,12a,12b,13,14,14a-tetradecahydropicen-3-yl dihydrogen phosphate;
and pharmaceutically acceptable salts thereof.

19. A pharmaceutical composition comprising a pharmaceutically acceptable carrier and at least one chemical entity of claim 1.

20. A pharmaceutical composition of claim 19 wherein the composition is formulated in a form chosen from tablets, capsules, powders, liquids, suspensions, suppositories, and aerosols.

21. A packaged pharmaceutical composition comprising a pharmaceutical composition of claim 19 and instructions for using the composition to treat a patient suffering from neoplastic diseases.

22. The packaged pharmaceutical composition of claim 21 wherein the disease is chosen from cancer.

23. A method of treating or ameliorating a neoplastic diseases in a mammal which method comprises administering to a mammal in need thereof a therapeutically effective amount of at least one chemical entity of claim 1.

24. A method of claim 23 wherein said neoplastic disease is chosen from lung cancer, breast cancer, liver cancer, kidney cancer, prostate cancer, melanoma, brain cancer, pancreatic cancer or hematologic cancer.

* * * * *